United States Patent [19]

Bolliger et al.

[11] Patent Number: 4,547,500

[45] Date of Patent: Oct. 15, 1985

[54] ERGOT PEPTIDE DERIVATIVES, THEIR PREPARATION AND PHARMACEUTICAL COMPOSITIONS CONTAINING THEM

[75] Inventors: Georg Bolliger, Binningen, Switzerland; Peter Stütz, Vienna, Austria

[73] Assignee: Sandoz Ltd., Basle, Switzerland

[21] Appl. No.: 493,335

[22] Filed: May 10, 1983

Related U.S. Application Data

[63] Continuation of Ser. No. 340,913, Jan. 20, 1982, abandoned, which is a continuation-in-part of Ser. No. 158,553, Jun. 11, 1980, abandoned.

[30] Foreign Application Priority Data

| Jun. 12, 1979 | [CH] | Switzerland | 5476/79 |
| Jun. 12, 1979 | [CH] | Switzerland | 5477/79 |
| Jun. 12, 1979 | [CH] | Switzerland | 5478/79 |
| Jun. 12, 1979 | [CH] | Switzerland | 5479/79 |

[51] Int. Cl.[4] .................. A61K 31/48; A61K 31/495; C07D 519/02
[52] U.S. Cl. .................................. 514/250; 544/346; 546/69
[58] Field of Search ....................... 544/346; 424/261; 340/913

[56] References Cited

U.S. PATENT DOCUMENTS

| 3,752,814 | 8/1973 | Fluckiger et al. | 544/346 |
| 3,901,891 | 8/1975 | Fehr et al. | 544/316 |
| 4,091,099 | 5/1978 | Fehr et al. | 544/346 |
| 4,321,381 | 3/1982 | Mantegani et al. | 546/67 |

FOREIGN PATENT DOCUMENTS

588485 6/1977 Switzerland ......... 544/346

OTHER PUBLICATIONS

Bernardi et al., La Chimica e L'Industria, vol. 54, pp. 998-999 (1972).

Berde et al., ed., Ergot Alkaloids and Related Compounds, (Springer-Verlag, New York, 1978), pp. 1-5, 40-44 and 69-73.

Primary Examiner—Alton D. Rollins
Attorney, Agent, or Firm—Gerald D. Sharkin; Robert S. Honor; Thomas O. McGovern

[57] ABSTRACT

A 2-methyl-8 (R) or (S) ergot peptide alkaloid in free base form or in pharmaceutically acceptable acid addition salt form is a useful anti-Parkinson agent, prolactin secretion inhibitor, anti-depressant, vigilance-increasing agent, and anti-migraine agent.

5 Claims, No Drawings

ERGOT PEPTIDE DERIVATIVES, THEIR PREPARATION AND PHARMACEUTICAL COMPOSITIONS CONTAINING THEM

This is a continuation of application Ser. No. 340,913, filed Jan. 20, 1982, which in turn is a continuation-in-part of Ser. No. 158,553, filed June 11, 1980, now abandoned.

This invention relates to ergot peptide derivatives, their preparation and pharmaceutical compositions containing them.

As is known, ergot peptide alkaloids may be natural products, modified natural products or be only obtainable by synthetic procedures. Swiss Pat. No. 588,485 discloses the synthesis of a large class of pharmacologically active 7-ergolene-8-carboxylic acid esters and amides, including amides containing a peptide moiety such as the cyclic tripeptide moieties in ergopeptines. The 7-ergolene moiety may be substituted in the 2 position, inter alia, by methyl. These methyl compounds are disclosed as being prepared from the corresponding 8(R) ergoline esters and amides. There is no suggestion in the Swiss Patent that these 8(R) ergoline derivatives have any use other than as intermediates.

We have now found that 2-methyl-8(R) and (S) ergot peptide alkaloids, which are nowhere specifically described in or suggested by this Swiss patent, have surprisingly a notable pharmacological profile.

The present invention accordingly provides a 2-methyl-8(R) or (S) ergot peptide alkaloid.

These compounds are hereinafter referred to as compounds of the present invention.

It is to be appreciated that in these compounds the remaining positions of the ergot cyclic peptide alkaloid may be substituted or unsubstituted. Conveniently the ergot moiety has a double bond in the 9,10 position.

The present invention further provides a compound of formula I

I wherein
$R_1$ is $(C_{1-4})$alkyl,
$R_2$ is $(C_{1-6})$alkyl or benzyl,
$R_3$ and $R_4$, independently, are hydrogen or $(C_{1-4})$alkyl,
$R_5$ is hydrogen or bromine, and
$R_6$ and $R_7$ are together a single bond,
$R_6$ and $R_7$ are each hydrogen, or
$R_6$ is methoxy and $R_7$ is hydrogen with the proviso that when $R_5$ is bromine, $R_7$ is hydrogen.

$R_1$ is conveniently methyl and especially isopropyl. $R_2$ is conveniently benzyl or preferably branched alkyl e.g. of 3 or 4 carbon atoms. $R_3$ conveniently is n- or isopropyl and preferably is methyl. $R_4$ is conveniently hydrogen. $R_5$ is preferably hydrogen. $R_6$ and $R_7$ conveniently form a single bond.

It is to be appreciated that the side chain in the 8 position of the ergot moiety may be in the $\alpha$ or $\beta$ configuration.

The present invention in another aspect provides a process for the production of a compound of the present invention which comprises (a) condensing an acid addition salt of an appropriate aminocyclol with a reactive acid derivative of a corresponding 2-methyl lysergic acid, (b) reducing an appropriate ergot peptide alkaloid substituted in the 2 position with a reducible dithiomethine or thiomethylene radical capable of being reduced to a methyl group, or (c) introducing a methyl group into the 2 position of an appropriate ergot cyclic peptide alkaloid unsubstituted in the 2 position.

The present invention also provides a process for the production of a compound of formula I as defined above which comprises (a) condensing an acid addition salt of a compound of formula II

II wherein $R_1$ and $R_2$ are as defined above with a reactive acid derivative of a compound of formula III

III wherein $R_3$ to $R_7$ are as defined above, (b) reducing a compound formula IV

IV wherein $R_1$ to $R_7$ are as defined above, and $R_8$ is a radical capable of being reduced to methyl, of formula V $$-CHR_{10}-S-R_9 \quad \quad V$$

wherein

R$_{10}$ is hydrogen or a radical —S—R$_{11}$ wherein R$_{11}$ is lower alkyl or a benzyl radical, and R$_9$ is lower alkyl or a benzyl radical, or R$_{10}$ is a radical —S—R$_{12}$ and R$_{12}$ together with R$_9$ is a radical of formula —(CH$_2$)$_n$— wherein n is 2 or 3, —CH$_2$—S—CH$_2$—, or

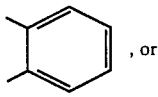, or (c) introducing a methyl group into the 2 position of a compound of formula VI

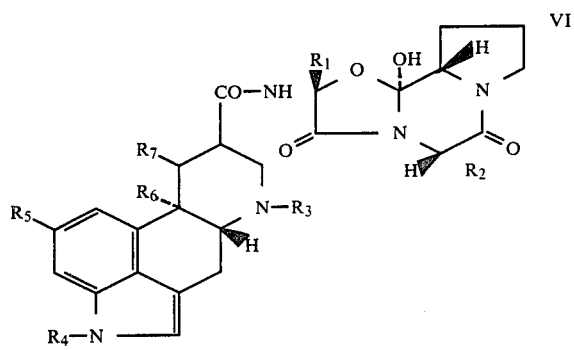

wherein R$_1$ to R$_7$ are as defined above.

Process (a) may be effected in conventional manner for the production of analogous ergot peptide alkaloids by condensation to form the amide bond between the ergot moiety and the aminocyclol.

Conveniently the acid addition salt of the aminocyclol is the hydrochloride. An appropriate reactive acid derivative of the 2-methyl lysergic acid is for example the acid chloride, the acid azide, or a mixed anhydride formed from sulphuric acid or trifluoroacetic acid.

Alternatively the reactive acid derivative may be the addition product produced by treating the 2-methyl lysergic acid with dimethylformamide or acetamide and thionyl chloride, phosgene, or oxalyl chloride.

Preferably the reaction is effected in the presence of triethylamine or pyridine. Suitable solvents include, for example, chloroform, methylene chloride, dimethylformamide, or acetonitrile.

The reaction is preferably effected at a temperature of from about —30° C. to about +20° C.

Process (b) may be effected in conventional manner for analogous reductions, e.g. using catalytic conditions, particularly using Raney-Nickel of moderate activity as catalyst e.g. Raney Nickel W.6.. The reaction may be effected in solution, e.g. in a mixture of acetone/dimethylformamide.

If the catalyst is pre-treated with solvent, the reduction may be effected at room temperature. Otherswise a slightly elevated reaction temperature e.g. up to 50° C. may be appropriate. It is preferred to use low temperatures when the ergot moiety has a 9,10 double bond in order to minimize saturation of this double bond.

In order to obtain a suitable catalyst to operate satisfactorily at low temperature Raney-Nickel W6 catalyst may be pre-treated by treating an aqueous suspension of Raney-Nickel W6 with an acetone/dimethylformamide mixture under stirring until dilution of a sample of the supernatant liquid with methylene chloride to twice to three times its volume does not cause any significant unclarity.

The reduction may be alternatively effected using appropriate reducing agents, e.g. sodium borohydride, lithium aluminium hydride and similar hydrides in the presence of metal salts, e.g. copper, zinc, titanium and nickel salts, in protic or aprotic solvents. A particularly suitable reducing agent is nickel boride, produced in situ, in ethylene glycol.

Preferred radicals R$_8$ include the 1,3-dithian-2-yl radical. Alternatively the 2-(1,3)-dithiolano radical is preferred.

Process (c) may be effected in conventional manner for such methylations in analogous compounds, e.g. in a two-step reaction. For example, 9,10-dihydroergot peptide alkaloids may be substituted in the 2 position by an aminomethyl radical, and then hydrogenated.

Preferably the introduction of the methyl radical is effected in two steps, the second step of which is the same as process (b). The first step of the reaction may be effected in analogous manner to the production of the starting materials for process (b) described below.

The starting materials of formula IV may be produced by condensing an acid addition salt of a compound of formula II as defined above with a reactive acid derivative of formula VII

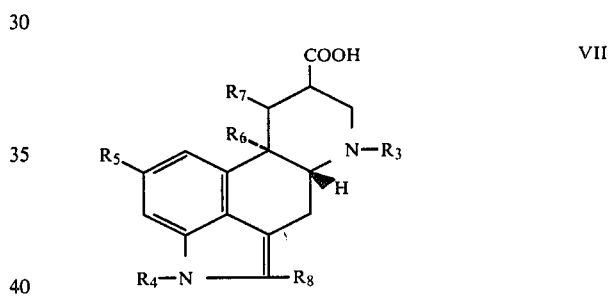

wherein R$_3$ to R$_8$ are as defined above, for example, in analogous manner to process (a).

Compounds of formula VII may for example be produced by reacting a compound of formula VIII

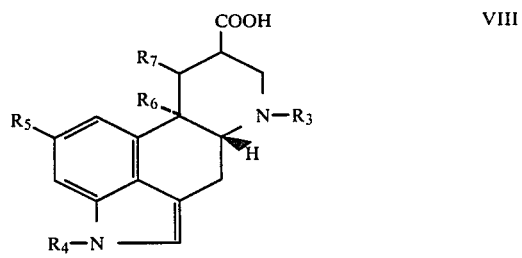

wherein R$_3$ to R$_7$ are as defined above with a compound of formula IX

L—R$_8$    IX wherein R$_8$ is as defined above and L is leaving group. The reaction may be effected in the presence of a Lewis acid, e.g. titanium trichloride. The leaving group may be e.g. chlorine, lower alkoxy, or a radical of formula X

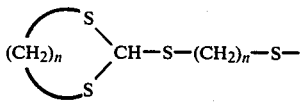

wherein n is as defined above.

The reaction may be effected in an inert solvent, e.g. chloroform or methanol. Suitable reaction temperatures are from about −10° to about +40° C.

The compounds of formula IX may be, for example, 2-methoxy-1,3-dithiolane, 2-chloro-1,3-dithiane, or 1,2-bis-(1,3-dithiolan-2-ylthio)ethane. The first two compounds are conveniently produced in situ. The use of in situ 2-chloro-1,3-dithiane (see J.Org.Chem. 44 (1979) 1847) facilitates the introduction of the 1,3-dithianyl moiety under mild conditions and without Lewis acids. For the other two compounds a Lewis acid is conveniently used.

A compound of formula IV may alternatively be produced by reacting an appropriate ergot alkaloid with a compound of formula IX as defined above, e.g. 2-chloro-1,3-dithiane, but in the absence of a Lewis acid [see Example 18].

Insofar as the production of any starting material is not particularly described then these are known or may be produced in known manner or in analogous manner to that described herein. In particular starting materials for process (b) other than compounds of formula IV may be produced in analogous manner to that described above for the production of compounds of formula IV.

The compounds of the invention may be isolated from the reaction mixture, and purified, in conventional manner. When the ergot moiety has a double bond in the 9,10 position, isomerization may occur at the 8 position, particularly when contact with polar aprotic solvents.

Mixtures of 8R and 8S isomers may be separated in conventional manner, for example, by chromatography. If desired, these 8R and 8S compounds may be epimerized in conventional manner, e.g. by treating with 2N sulphuric acid.

Free base forms of the compounds of the invention may be converted into acid addition salt forms in conventional manner, and vice versa. Suitable salts for acid addition formation include, for example, hydrochloric acid, maleic acid, sulphuric acid, fumaric acid and tartaric acid.

In the following examples all temperatures are in degrees Centigrade and are uncorrected.

EXAMPLE 1

2-methyl-α-ergocryptine and
2-methyl-α-ergocryptinine (process a)

2.82 g (10 mMol) anhydrous 2-methyl lysergic acid are dissolved in 25 ml absolute dimethylformamide on the addition of 2.28 g (20 mMol) trifluoroacetic acid, and with stirring brought to −10° C. At this temperature, a mixture of 2.52 g (12 mMol) trifluoroacetic acid anhydride in 12 ml absolute acetonitrile is added dropwise and the resultant clear solution is stirred for 10 minutes. 12 ml pyridine and 1.81 g (5 mMol) (2R,5S,10aS,10bS)-2-amino-5-isobutyl-10b-hydroxy-2-isopropyl-octahydro-3,6-dioxo-8H-oxazolo[3,2-a]pyrrolo[2,1-c]pyrazine hydrochloride are added and the reaction mixture is stirred for 1 hour at between −10° and 0°.

To work up, 200 ml methylene chloride is added and the mixture is well shaken with 100 ml 2N sodium carbonate solution. The organic phase is separated and the aqueous phase is washed three times with 100 ml methylene chloride. The combined organic phase are dried over sodium sulphate and concentrated in a vacuum. The residue is chromatographed on silicagel eluted with 2% methanol in methylene chloride to give pure 2-methyl-α-ergocryptinine. M.pt. 225°–227° (decomp) from methylene chloride/ether; $[\alpha]_D^{20} = +412°$ (c=0.4 in chloroform).

Elution with 3% methanol in methylene chloride yielded 2-methyl-α-ergocryptine. The hydrogen fumarate is obtained by reaction with 1 equivalent of fumaric acid. M.pt. 181°–184° (decomp) $[\alpha]_D^{20} = +25.0$ (c=0.2 in ethanol).

The following compounds are produced in analogous manner to Example 1.

EXAMPLE 2

2-methyl-ergotaminine

Crystallization from methylene chloride/ether. M.pt. 219°–221° (decomp); $[\alpha]_D^{20} = +398°$ (c=1.0 in chloroform).

EXAMPLE 3

2-methyl-ergotamine

Crystallization from methylene chloride/benzene. M.pt. 169°–171° (decomp); $[\alpha]_D^{20} = -100°$ (c=1.0 in chloroform).

EXAMPLE 4

1,2-dimethyl-ergotamine

Crystallization as the hydrogen tartrate from abs. ethanol. M.pt. 178°–179° (decomp); $[\alpha]_D^{20} = +44°$ (c=1.0 in dimethyl formamide).

EXAMPLE 5

2-methyl-6-nor-6-isopropyl-9,10-dihydroergotamine

Crystallization from methanol. M.pt. 172° (decomp); $[\alpha]_D^{20} = -60.2°$ (c=1.3 in methylene chloride).

EXAMPLE 6

2-methyl-9,10-dihydro-β-ergocryptine

Crystallization from methylene chloride/ether. M.pt. 187°–190° (decomp); $[\alpha]_D^{20} = -3.8°$ (c=0.4 in chloroform).

EXAMPLE 7

2-methyl-9,10-dihydroergotamine

Crystallization from methylene chloride/ethyl acetate. M.pt. 185°–186° (decomp); $[\alpha]_D^{20} = -77.5°$ (c=1.0 in pyridine).

EXAMPLE 8

2-methyl-9,10-dihydroergocristine

Crystallization as the hydrogen fumarate from methylene chloride/ethyl acetate. M.pt. 191°–192°; $[\alpha]_D^{20} = -13.9°$ (c=0.6 in methanol).

EXAMPLE 9

2-methyl-9,10-dihydro-ergonine

Crystallization from methylene chloride/benzene. M.pt. 174°–176° (decomp); $[\alpha]_D^{20} = -57°$ (c=0.1 in pyridine).

EXAMPLE 10

2-methyl-9,10-dihydro-ergocornine

Crystallization from methylene chloride/benzene. M.pt. 172°–174° (decomp); $[\alpha]_D^{20} = -58°$ (c=1.0 in pyridine).

EXAMPLE 11

2-methyl-9,10-dihydro-α-ergocryptine

Crystallization from methylene chloride/ether. M.pt. 179°–182° (decomp); $[\alpha]_D^{20} = 2.4°$ (c=0.55 in chloroform).

EXAMPLE 12

2-methyl-2'β-isopropyl-5'α-n-butyl-ergopeptine

Crystallization as the hydrogen fumarate from ethyl acetate/acetone. M.pt. 157°–160° (decomp); $[\alpha]_D^{20} = +54.0°$ (c=0.55 in dimethylformamide).

EXAMPLE 13

2-methyl-ergocristine

Crystallization from methylene chloride/isopropylether. M.pt. 165°–168° (decomp); $[\alpha]_D^{20} = +40.9°$ (c=0.45 in dimethylformamide).

EXAMPLE 14

2-methyl-β-ergocryptine

Crystallization from methylene chloride/isopropylether. M.pt. 177°–180° (decomp); $[\alpha]_D^{20} = +30.0°$ (c=0.53 in dimethylformamide).

EXAMPLE 15

2-methyl-ergocornine

Crystallization as the hydrogen fumarate from ethyl acetate/ethanol. M.pt. 186°–189° (decomp); $[\alpha]_D^{20} = +40.7°$ (c=0.59 in dimethylformamide).

EXAMPLE 16

2-methyl-6-demethyl-2'β-isopropyl-5'α-isobutyl-ergopeptine

Crystallization from methylene chloride/ether. M.pt. 172°–175° (decomp); $[\alpha]_D^{20} = +60.0°$ (c=0.21 in dimethylformamide).

EXAMPLE 17

2-methyl-6-demethyl-6-ethyl-2'β-isopropyl-5'α-isobutyl-ergopeptine

Crystallization as the hydrogen sulfate from ethyl acetate/ether. M.pt. 142°–147° (decomp); $[\alpha]_D^{20} = +43.2°$ (c=0.45 in dimethylformamide).

EXAMPLE 18

2-methyl-α-ergocryptine (process b or c)

(a) 2-(1,3-dithian-2-yl)-α-ergocryptine

A solution of 11.5 g (20 mMol) of α-ergocryptine in absolute chloroform or methylene chloride is added dropwise quickly to a vigorously stirred solution of about 1.2 equivalents of 2-chloro-1,3-dithiane in absolute chloroform or methylene chloride, cooled to −15°. The reaction mixture is allowed to warm to 5° to 10° resulting in a black dirty precipitate. The mixture is stirred at 10° and worked up. Working up comprises making the mixture alkaline with 2N sodium carbonate solution and extracting with methylene chloride/methanol (9:1). The organic phases are washed with saturated sodium hydrogen carbonate solution, dried over sodium sulphate, filtered and evaporated. 16.7 g of a foam containing the heading compound is obtained which can be used further as such or else chromatographed on silicagel using 2% CH₃OH in CH₂Cl₂ as eluant to yield the heading compound. The hydrogen maleate of the heading compound has M.pt 163°–165° (from ethyl acetate/ether); $[\alpha]_D^{20} = +111°$ (c=0.55 in dimethylformamide).

(b) 2-methyl-α-ergocryptine 23 ml of an aqueous suspension of Raney Nickel W6 is pretreated with increasing amounts of 2 liters acetone/dimethylformamide (7:3) solution under stirring. Samples of the supernatant liquid are taken as the acetone/dimethylformamide is added. When the sample on treatment with methylene chloride yields no unclarity, then the addition of acetone/dimethylformamide is stopped.

7.5 g of 2-(1,3-dithian-2-yl)-α-ergocryptine in 150 ml acetone containing 20% dimethylformamide are treated with 105 ml of this treated Raney Nickel W6 in 100 ml of the same solvent. After 15 minutes, the catalyst is filtered off and it is washed several times with about 300 ml of the solvent mixture. The solvent is distilled from the combined organic phases to give a brown foam which is taken up in ethanol and reacted with fumaric acid (1 equivalent) to give the hydrogen fumarate of the heading compound. M.pt. 181°–184° (decomp); $[\alpha]_D^{20} = +25.1$ (c=0.2 ethanol).

In analogous manner, the title compounds of Examples 2 to 17 may be produced.

EXAMPLE 19

2-methyl-6-nor-6-isopropyl-9,10-dihydro-ergotamine (process b)

(a) 2-[2-(1,3)-dithiolane]-6-nor-6-isopropyl-9,10-dihydro-ergotamine 60 ml absolute dimethylformamide at −20° are treated dropwise with 2.7 g oxalyl chloride in 8.5 ml acetonitrile, and then with 7.1 g (17.7 ml mMol) dry 2-[2-(1,3)-dithiolano]-6-nor-6-isopropyl-9,10-dihydrolysergic acid, resulting in a dark brown precipitate. The mixture is cooled to 0° for 30 minutes, diluted with 18 ml absolute pyridine and treated with 3.24 g (8.8 mMol) (2R,5S,10aS,10bS)-2-amino-5-benzyl-10b-hydroxy-2-methyl-octahydro-3,6-dioxo-8H-oxazolo[3,2-a]-pyrrolo[2,1-c]pyrazine hydrochloride. The mixture is stirred vigorously for 2 hours at −10° and allowed to warm to 0°.

To work up, the mixture is treated with citrate buffer pH4, and made alkaline with 2N sodium carbonate solution. After extraction with methylene chloride, drying and concentration of the methylene chloride extracts, chromatography on silicagel yields the heading compound which is used further as such.

(b) 2-methyl-6-nor-6-isopropyl-9,10-dihydroergotamine 3.8 g sodium borohydride in 50 ml water is slowly dropped into a solution of 3.58 (5 mMol) 2-[2-(1,3)-thiolano]-6-nor-6-isopropyl-9,10-dihydro-ergotamine and 11.9 g Nickel chloride hexahydrate in 120 ml of ethylene glycol. The mixture is warmed to 90° for 2 hours. The resultant black suspension is decanted and the filtrate extracted with methylene chloride.

The organic extracts are washed with water, dried and concentrated to give a whitish foam which is chromatographed on silicagel to give with 3% $CH_3OH$ in $CH_2Cl_2$ the heading compound. M.pt. 172° (decomp; from $CH_3OH$); $[\alpha]_D^{20} = -60.2°$ (c=1.3 in $CH_2Cl_2$).

In analogous manner the compounds of Examples 1 to 4 and 6 to 17 may be produced.

In analogous manner to that disclosed in Example 1, an 8S compound of formula I wherein $R_1$ is ethyl, $R_2$ is n-butyl, $R_3$ is hydrogen, $R_4$ is n-butyl, $R_5$ is bromine, $R_6$ is methoxy and $R_7$ is hydrogen, may be produced.

The compounds of the invention are useful pharmaceuticals because they exhibit pharmacological activity in animals.

The compounds of the invention are useful as antiparkinson agents, e.g. for the treatment of Morbus Parkinson as indicated by a dopaminergic stimulating effect in standard aninal tests. For example, the compounds when administered at from about 0.03 to about 3 mg/kg i.p. elicited contralateral rotations in the rat having unilateral degeneration of nigro-striatal dopamine pathway induced by injection of 6-hydroxydopamine into one substantia nigra [method according to U. Ungerstaedt Acta physiol. scand. Suppl. 387, 66–93 (1971)]. The compounds also exhibit stereotypy in the apomorphine stereotypy test in i.p. administration of about 30 mg/kg of the compound.

For this use the dosage will, of course, vary depending on the compound employed, mode of administration and treatment desired. However, in general, satisfactory results are obtained when administered at a daily dosage of from about 0.01 mg to about 30 mg per kg animal body weight, conveniently given in divided doses 2 to 4 times a day or in sustained release form. For the larger mammals, the total daily dosage is in the range from about 0.5 to about 100 mg, and dosage forms suitable for oral administration comprise from about 0.1 mg to about 50 mg of the compounds admixed with a solid or liquid pharmaceutical carrier or diluent.

The compounds of the invention are furthermore useful as prolactin secretion inhibiting agents, e.g. for the treatment of hyperprolactinemia, as indicated by standard tests e.g. by an inhibition of implantation in the rat on s.c. administration of from about 0.01 to about 1 mg/kg of the compounds and an inhibition of lactation on p.o. administration of from about 1 to about 10 mg/kg of the compounds.

For this use the dosage will, of course, vary depending on the compound employed, mode of administration and treatment desired. However, in general, satisfactory results are obtained when administered at a daily dosage of from about 0.01 mg to about 10 mg per kg animal body weight, conveniently given in divided doses 2 to 4 times a day or in sustained release form. For the larger mammals, the total daily dosage is in the range from about 0.5 to about 100 mg, and dosage forms suitable for oral administration comprise from about 0.1 mg to about 50 mg of the compounds admixed with a solid or liquid pharmaceutical carrier or diluent.

The compounds of the invention are furthermore useful as anti-depressant agents, as indicated by an inhibition of ptosis and catalepsy induced by reserpine in rats on s.c. administration of 1 to 50 mg/kg of the compounds. For this use the dosage will, of course, vary depending on the compound, mode of administration and treatment desired. However, in general, satisfactory results are obtained when administered at a daily dosage of from about 0.01 mg to about 50 mg per kg animal body weight, conveniently given in divided doses 2 to 4 times a day or in sustained release form. For the larger mammals, the total daily dosage is in the range from about 0.5 to about 100 mg, and dosage forms suitable for oral administration comprise from about 0.1 mg to about 50 mg of the compounds admixed with a solid or liquid pharmaceutical carrier or diluent.

The compounds of the invention are furthermore useful as vigilance increasing agents, e.g. for the treatment of cerebral insufficiency e.g. in geriatrics as indicated by an increase in the wake phase and a decrease in the paradoxical and classical sleep phases in the sleep/wake cycle test in the rat in p.o. administration of from about 1 to about 20 mg/kg of the compounds, and more preferably by an inhibition of pontogeniculo-occipital (PGO) waves (>100 microvolts) in the cat on i.v. administration of 0.01 to 1 mg/kg, in accordance with the method described by J. M. Vigouret et al, Pharmacology 16, (Suppl.1),156–173,(1978).

The compounds of the invention are furthermore useful for the treatment of migraine and orthostatic disorders, e.g. thrombosis prophylaxis, as indicated by a vasoconstricting effect in standard animal tests, e.g. in the Mellander-cat test [Angiologica 3, 77–99, (1966)] by an arterial vasotonic effect, on i.a. administration of from about 5 to about 45 µg/kg animal body weight.

For these two uses the dosage will, of course, vary depending on the compound employed, mode of administration and treatment desired. However, in general, satisfactory results are obtained when administered at a daily dosage of from about 1 µg to about 20 mg per kg animal body weight, conveniently given in divided doses 2 to 4 times a day or in sustained release form. For the larger mammals, the total daily dosage is in the range from about 0.5 to about 100 mg, and dosage forms suitable for oral administration comprise from about 0.1 mg to about 50 mg, of the compounds admixed with a solid or liquid pharmaceutical carrier or diluent.

The preferred utilities of the compounds of the invention are as prolactin secretion inhibition agents, antidepressants, and especially as vigilance increasing agents, and anti-parkinson agents.

The compounds 2-methyl-9,10-dihydro-α-ergocryptine and 2-methyl-α-ergocryptine show particularly interesting activity.

The compounds of formula I may be administered in similar manner to known standards for use in these activities for example, L-dopa for the anti-parkinson indication. The suitable daily dosage for any particular compound will depend on a number of factors such as its relative potency of activity in the above-described tests. In the Ungerstedt test described above L-dopa induces about 2000 rotations over 7 hours on administration of 25 mg/kg i.p. The preferred compound of the invention exhibits the same order of activity at a dose of 1 mg/kg i.p.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent.

Such compositions conveniently contain more than 1% by weight of the compound of the invention and may be prepared by conventional techniques to be in conventional forms, for example, capsules, tablets, suppositories, dispersible powders, syrups, elixirs, suspensions or solutions, for enteral or parenteral administration. 2-methyl-α-ergocryptine and the other ergolenes of the present invention are preferably administered in solid form. Suitable pharmaceutical diluents or carriers are those compatible with ergot alkaloids and include, for example, water, alcohols, cellulose, calcium phosphate, and lactose as well as suitable preserving agents, such as ethyl-p-hydroxy-benzoate, suspending agents such as methyl cellulose and wetting agents such as polyoxyethylene stearate and polyoxyethylene sorbitan mono-oleate, granulating and disintegrating agents such as starch and cellulose, binding agents such as methylcellulose, starch and polyvinylpyrrolidone and lubricating agents such as magnesium stearate, stearic acid and talc, in order to provide an elegant and palatable pharmaceutical preparation. Compositions in tablet form may be coated by conventional techniques to delay desintegration of the tablet and absorption of the active ingredient in the gastric-intestinal tract and thereby provide sustained action over a long period.

| Tablet Composition | |
|---|---|
| Compound of formula I, e.g. 2-methyl-9,10-dihydro-ergotamine mesylate or 2-methyl-α-ergocryptine hydrogen fumarate | 1.025 mg |
| Tartaric acid | 0.5 mg |
| Lactose | 119.425 mg |
| Corn starch | 18.0 mg |
| Silicion dioxide | 0.35 mg |
| Magnesium stearate | 0.7 mg |

The resultant composition is pressed into a 140 mg tablet.

| Capsule Composition | |
|---|---|
| Compound of formula I, e.g. 2-methyl-9,10-dihydro-ergotamine or 2-methyl-α-ergocryptine hydrogen fumarate | 1 mg |
| Lactose | 80.75 mg |
| Corn starch | 60.0 mg |
| Tartaric acid | 1.0 mg |
| Silicion dioxide | 0.75 mg |
| Magnesium stearate | 1.5 mg |

The composition is filled into a hard gelatine capsule.

In one group of compounds of formula I $R_2$ is $(C_{1-4})$alkyl or benzyl, and $R_5$ is hydrogen or bromine with the proviso that (i) when $R_5$ is bromine $R_6$ and $R_7$ are each hydrogen, and (ii) when $R_5$, $R_6$ and $R_7$ are each hydrogen, $R_3$ is hydrogen or $(C_{2-4})$alkyl.

In a second group of compounds of formula I $R_2$ is $(C_{1-4})$alkyl or benzyl, $R_3$ is methyl, and $R_5$, $R_6$ and $R_7$ are each hydrogen.

In a third group of compounds of formula I $R_5$ is hydrogen and $R_6$ and $R_7$ together form a bond or $R_6$ and $R_7$ each are hydrogen.

In a fourth group of compounds $R_3$ is other than methyl when $R_5$, $R_6$ and $R_7$ are each hydrogen, and the 8 carbon atom in the ergot moiety has the R configuration.

In a fifth group of compounds $R_3$ is methyl and $R_5$, $R_6$ and $R_7$ are each hydrogen and the 8 carbon atom in the ergot moiety has the R configuration.

The compound of Example 18 exhibits particularly interesting properties.

What we claim is:

1. 2-Methyl-α-ergocryptine.

2. A method of treating cerebral insufficiency, depression, or Parkinsonism or inhibiting prolactin secretion in animals which comprises administering a therapeutically effective amount of a compound of claim 1 to an animal in need of such treatment.

3. A pharmaceutical composition for the treatment of cerebral insufficiency, depression or Parkinsonism or for inhibiting prolactin secretion comprising a therapeutically effective amount of a compound of claim 1 in association with a pharmaceutical carrier or diluent.

4. A pharmaceutical composition for increasing vigilance comprising a vigilance increasing effective amount of a compound of claim 1 in association with a pharmaceutically acceptable carrier or diluent.

5. A method of increasing vigilance in animals which comprises administering a vigilance increasing effective amount of a compound of claim 1 to an animal in need of said treatment.

* * * * *